United States Patent [19]

Mineta et al.

[11] Patent Number: 5,275,757
[45] Date of Patent: Jan. 4, 1994

[54] LIQUID CRYSTAL COMPOUNDS AND LIQUID CRYSTAL DISPLAY DEVICES

[75] Inventors: Hiroshi Mineta, Tsukuba; Tomoyuki Yui, Nagareyama; Takahiro Matsumoto, Tsukuba, all of Japan

[73] Assignee: Mitsubishi Gas Chemical Company, Inc., Tokyo, Japan

[21] Appl. No.: 985,319

[22] Filed: Dec. 4, 1992

[30] Foreign Application Priority Data

Dec. 6, 1991 [JP] Japan .................... 3-349097

[51] Int. Cl.$^5$ ............... C09K 19/34; C07D 319/06; C07C 69/76; G02F 1/13
[52] U.S. Cl. ............... 252/299.61; 252/299.67; 359/103; 549/375; 560/76; 560/87; 560/107; 560/111
[58] Field of Search ............... 252/299.01, 299.61, 252/299.67; 359/10, 3549.375, 560.76, 87.107, 111 359/103; 549/375; 560/76, 87, 107, 111

[56] References Cited

U.S. PATENT DOCUMENTS

5,046,823 10/1991 Mori et al. ............... 359/56
5,171,471 12/1992 Suzuki et al. ............... 252/299.61

FOREIGN PATENT DOCUMENTS

0332392 9/1989 European Pat. Off. .

Primary Examiner—Robert L. Stoll
Assistant Examiner—Shean C. Wu
Attorney, Agent, or Firm—Sherman and Shalloway

[57] ABSTRACT

Novel anti-ferroelectric liquid crystal compounds represented by the following general formula (I) and a liquid crystal display element wherein such a compound is used.

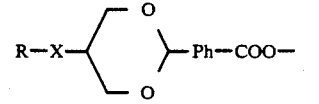

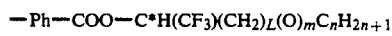

Ph represents a phenylene group,
R represents a straight-chain alkyl group having 6 to 10 carbon atoms,
X represents an oxygen atom or a single bond provided that when X is an oxygen atom, L is an integer of 5 to 8, m is 1 and n is an integer of 1 to 7, or L and m are zero (0) and n is an integer of 6 to 8, and when X is a single bond,
L is an integer of 5 to 8, m is 1 and n is an integer of 1 to 7, and
C* represents an asymmetric carbon atom.

6 Claims, 5 Drawing Sheets

LIQUID CRYSTAL COMPOUNDS AND LIQUID CRYSTAL DISPLAY DEVICES

DETAILED DESCRIPTION OF THE INVENTION

1. Industrially Applicable Field

This invention relates to novel liquid crystal compounds and liquid crystal display elements. More specifically, this invention relates to novel dioxane anti-ferroelectric liquid crystal compounds and a liquid crystal display element wherein such a compound is used.

2. Prior Art

Liquid crystal display elements have so far been utilized in various small-sized display elements due to reasons of low voltage workability and low electric power consumption and the reason that thin-sized display is possible and other reasons. However, in accordance with recent enlargement of uses of liquid display device, for example application thereof to the information field, the OA-related instrument field or the television field, high performance large-sized liquid crystal display device having a display capacity and a display quality exceeding those of the usual CRT display device have rapidly come to be required. However, insofar as existent nematic liquid crystals are used as a display device, it is not easy to make large sized display or low in costs due to complication of production processes and lowness of yields, even when they are active maxtrixdrive liquid crystal display device. On the other hand, in case of STN-type liquid crystal display device, large capacity drive is not always easy, and further, there are limitations in response time and video rate display is difficult. Therefore, it is the present state of things that it is hard to say that nematic liquid crystal display device satisfy requirements for the above high performance and large-sized liquid crystal display device.

PROBLEMS TO BE SOLVED BY THE INVENTION

On the other hand, a liquid crystal display device using a ferroelectric liquid crystal substance is drawing attention as a liquid crystal display device exhibiting high speed response. A surface stabilized ferroelectric liquid crystal (SSFLC) device published by N. A. Clark and S. T. Lagerwall is drawing attention in that it has a high speed response and a wide viewing angle not so far obtained and it has memorizability, and by other reasons [N. A. Clark and S. T. Lagerwall, Appl. Phys. Lett. 36 (1980) 899].

Switching characteristics of this SSFLC have detailedly been studied, and many ferroelectric liquid crystal substances have been proposed to optimize various performance necessary for devices. However, there are various problems, for example that the threshold characteristics of the liquid crystal are insufficient, contrast is not good partly because the structure of the liquid crystal layer is chevron structure, high speed response is not put into practice, realization of bistability, one of the maximum characteristics of SSFLC, is not easy because of difficulty of control of alignment of the liquid crystal, and alignment of the liquid crystal is destroyed by mechanical shock and its recovery is difficult, and it is the present state of things that since no ferroelectric liquid crystal substance capable of solving these problems has yet been found, such an element has not yet been put to practical use.

Separately therefrom, development of devices having a switching mechanism different from that of SSFLC has been advanced at the same time. Tristable switching of a liquid crystal substance having an anti-ferroelectric phase (hereafter referred to as an anti-ferroelectric liquid crystal substance) is one of these new switching mechanism (refer to Japanese Journal of Applied Physics, vol. 27, pp. L729, 1988). An anti-ferroelectric liquid crystal substance used in an anti-ferroelectric liquid crystal has three stable states. Namely, in an anti-ferroelectric liquid crystal substance exist not only two uniform states (Ur, Ul) seen in a ferroelectric liquid crystal substance but the third stable state (the third state). Chandani et al. report that this third state is the anti-ferroelectric phase (refer to Japanese Journal of Applied Physics, vol. 28, pp. L1261, 1989 and Japanese Journal of Applied Physics, vol. 28, pp. L1265, 1989). Such tristable switching is the first characteristic of an anti-ferroelectric liquid crystal substance. The second characteristic of an anti-ferroelectric liquid crystal substance is that a clear threshold exists against applied voltages. The third characteristic of an anti-ferroelectric liquid crystal substance is that it has memory effect. By using an anti-ferroelectric liquid crystal substance having these excellent characteristics, it is possible to realize a liquid crystal display device having a rapid speed response and extremely good contrast.

Further, it is mentioned as another large characteristic of an anti-ferroelectric liquid crystal substance that the layer structure of the liquid crystal is readily switched by an electric field (Japanese Journal of Applied Physics, vol. 28, pp. L119, 1989 and Japanese Journal of Applied Physics, vol. 29, pp. L111, 1990). Thereby, it become possible to make a liquid crystal display element having only extremely a few drawbacks and having an ability to self-repair the orientation, and it is possible to realize a liquid crystal element excellent in contrast. As anti-ferroelectric liquid crystal substances are known those disclosed in Japanese Laid-Open Patent Publication Nos. 213390/1989, 316339/1989, 316367/1989, 316372/1989 and 28128/1990 and Liquid Crystals, vol. 6, pp. 167, 1989. The history of studies on anti-ferroelectric liquid crystal substances is short and the number of anti-ferroelectric liquid crystal substances so far known is not large compared to ferroelectric liquid crystal substances, but the number is gradually increasing in accordance with advance of studies. When anti-ferroelectric liquid crystal substances so far prepared are investigated from the aspect of response speed, many of them do not have an sufficiently rapid response speed, and the number of anti-ferroelectric liquid crystal substances applicable for highly precise display devices is not yet so large. Thus this point was a somewhat disadvantageous aspect compared to usual ferroelectric liquid crystal substances. Therefore, it is extremely advantageous for realization of high precise display devices if there can be provided anti-ferroelectric liquid crystal substances having an extremely rapid response speed around room temperature. This invention has been attained under such demand, and provides novel anti-ferroelectric liquid crystal substances extremely excellent high speed response around room temperature.

Thus the first object of this invention is to provide novel liquid crystal compounds having an anti-ferroelectric phase.

The second object of this invention is to provide liquid crystal compounds having tristable switching, clear threshold characteristics and good memory effect and usable as a liquid crystal display device.

The third object of this invention is to provide high performance liquid crystal compounds having high speed response and usable in large-sized liquid crystal display devices.

Another object of this invention is to provide liquid crystal compounds exhibiting an extremely rapid response speed at a temperature of the order of room temperature and exhibiting anti-ferroelectricity.

Still another object of this invention is to provide a liquid crystal display device wherein a liquid crystal compound having the above characteristics is used.

Still another object of this invention will be more apparent by the following description.

MEANS FOR SOLVING THE PROBLEMS

According to researches by the present inventors, it was found that the above objects and advantages of this invention could be attained by novel anti-ferroelectric liquid crystal compounds represented by the following general formula (I)

$-Ph-COO-C^*H(CF_3)(CH_2)_L(O)_mC_nH_{2n+1}$

Ph represents a phenylene group,
R represents a straight-chain alkyl group having 6 to 10 carbon atoms,
X represents an oxygen atom or a single bond provided that when X is an oxygen atom, L is an integer of 5 to 8, m is 1 and n is an integer of 1 to 7, or L and m are zero (0) and n is an integer of 6 to 8, and when X is a single bond,
L is an integer of 5 to 8, m is 1 and n is an integer of 1 to 7, and
C* represents an asymmetric carbon atom.

Hereafter, the liquid crystal compounds of this invention are described in more detail.

The liquid crystal compounds of this invention are dioxane compounds represented by the above general formula (I).

In the general formula (I), Ph represents a phenylene group, and preferred is 1,4-phenylene group

.

R represents a straight-chain alkyl group having 6 to 10 carbon atoms. X represents an oxygen atom or a single bond. The values of L, m and n vary according to whether X is an oxygen atom or a single bond. Namely, when X is an oxygen atom, (i) L is an integer of 5 to 8, m is 1 and n is an integer of 1 to 7, or (ii) both L and m are zero and n is an integer of 6 to 8. When X is a single bond, L is an integer of 5 to 8, m is 1 and n is an integer of 1 to 7. C* represents an asymmetric carbon atom.

Among optically active alcohols used in preparation of the dioxane compounds of the above general formula (I) of this invention, for example 1,1,1-trifluoro-2-octanol can be a product on the market. Further, an optically active alcohol such as 1,1,1-trifluoro-7-ethoxy-2-heptanol can be prepared, for example according to the following reaction steps of (a) to (h).

Abbreviations in the above steps mean the following compounds and groups, respectively.
DHP: Dihydropyrane
THP: Tetrahydropyranyl group
TsCl: Paratoluenesulfonyl chloride
Ts: Paratoluenesulfonyl group.

Anti-ferroelectric liquid crystal compounds of this invention represented by the general formula (I) can be prepared according to various methods, and examples thereof represented by reaction formulae are as follows.

(A) In case of preparation of

(in case of X being a single bond)

(ii) $RCH(COOC_2H_5)_2 \xrightarrow{LiAlH_4} RCH(CH_2OH)_2$ (vi) $CH_3COO-Ph-COOH \xrightarrow{SOCl_2} CH_3COO-Ph-COCl$ (viii) $CH_3COO-Ph-COO-CH(CF_3)(CH_2)_L(O)_mC_nH_{2n+1} \xrightarrow{Ph-CH_2NH_2}$ $HO-Ph-COO-CH(CF_3)(CH_2)_L(O)_mC_nH_{2n+1}$  <2>

(ix) <1> + <2> ⟶ desired substance

(B) In case of preparation of

$R-\left\{\begin{array}{c}O\\O\end{array}\right\}-Ph-COO-Ph-COO-C^*H(CF_3)(CH_2)_L(O)_mC_nH_{2n+1}$ (in case of X being an oxygen atom)

(i) $CH_2\overset{O}{-\!\!-\!\!-}CHCH_2OH \xrightarrow{ROH/acid} ROCH(CH_2OH)_2$ (v) $HO-Ph-COO-CH(CF_3)(CH_2)_L(O)_mC_nH_{2n+1}$ + <3> ⟶ desired substance

EFFECT OF THE INVENTION

According to the thus described present invention, it is possible to provide novel anti-ferroelectric liquid crystal compounds. The novel anti-ferroelectric liquid crystal compounds provided by this invention exhibit an extremely high speed response of 20 to 30μ seconds around room temperature and further, have as their characteristics tristable switching, clear threshold characteristics and good memory effect, and thus can be utilized, by utilizing these characteristics, for making of liquid crystal display devices having excellent display functions.

EXAMPLES

This invention is further specifically described below according to examples and comparative examples, but it is a matter of course that this invention is not limited thereto.

EXAMPLE 1

Preparation of 4'-(1-trifluoromethyl-6-ethoxyhexyloxycarbonyl)phenyl ester of 4-(5-n-octyl-1,3-dioxan-2-yl)benzoic acid [the case of $R=n-C_8H_{17}$, $X=$single bond, $L=5$, $m=1$ and $n=2$ in the general formula (I)]

1) Preparation of diethyl octylmalonate 200 ml of ethanol was put in a 1-liter four-necked flask, 7.6 g of metal sodium cut into pieces was put therein portionwise to prepare sodium ethoxide. To this were added dropwise 54.6 g of diethyl malonate and then 63.9 g of octyl bromide. Thereafter, the mixture was refluxed for 3 hours. Then, the most part of ethanol was distilled away under the atmospheric pressure, 200 ml of water was added, and the mixture was extracted with 250 ml of ether. The ether solution was dried over sodium sulfate, ether was distilled away, and the residue was distilled under reduced pressure to give 72.1 g of a colorless oily substance (b.p. 111° C./2 mmHg). Yield 85%.

2) Preparation of 2-octyl-1,3-propanediol 250 ml of ether and 19.0 of lithium aluminum hydride were put in a 1-liter four-necked flask, and a solution obtained by dissolving 72.1 g of the thus prepared diethyl octylmalonate in 50 ml of ether was put therein dropwise at such a rate that ether is gently refluxed. After the dropwise addition, the mixture was refluxed with heating for 3 hours, and after allowing it to cool, a mixture of water-THF was added to decompose excess lithium aluminum hydride. The resultant solid was removed by filtration, and the filtrate was washed with saturated saline and dried over anhydrous sodium sulfate. The crude crystal obtained by distilling away the solvents was recrystallized from isooctane to give 32.4 g of colorless crystals. Yield 65%.

3) Preparation of 4-(5-octyl-1,3-dioxan-2-yl)benzonitrile

In a 500-ml egg-plant type flask were put 32.3 g of 2-octyl-1,3-propanediol, 22.5 g of p-cyanobenzaldehyde, 0.11 g of p-toluenesulfonic acid monohydrate and 300 ml of benzene, and the mixture was heated. The generated water was removed by azeotropy with benzene. Then, benzene was distilled away, and the residue was neutralized with aqueous saturated sodium bicarbonate solution. The mixture was extracted with dichloromethane, and the extract was washed with water and then dried over anhydrous sodium sulfate. Dichloromethane was distilled away to give a solid which was then recrystallized from isooctane to give 37.7 g of colorless crystals.

4) Preparation of 4-(5-octyl-1,3-dioxan-2-yl)benzoic acid

A condenser was attached to a 2-liter egg-plant type flask, 27.2 g of potassium hydroxide, 20 ml of water, 1 l of ethylene glycol and 36.6 g of the benzonitrile obtained in 3) were put therein, and the mixture was heated at 180° C. for 6 hours. The reaction mixture was acidified with 1N hydrochloric acid, and the deposited solid was filtered, washed with water, air dried, and recrystallized to give 17.5 g of the desired product benzoic acid derivative.

5) Preparation of 4-acetoxy-1-(1-trifluoromethyl-6-ethoxy-hexyloxycarbonyl)benzene 1.2 g of 4-acetoxy-acetic acid was added to 20 ml of thionyl chloride, and the mixture was subjected to reaction under reflux for 5 hours. Then, excess thionyl chloride was distilled away, and a mixture of 3 ml of pyridine, 20 ml of toluene and 0.6 g of R-(+)-1,1,1-trifluoro-7-ethoxy-2-heptanol was added dropwise. After the dropwise addition, the mixture was stirred at room temperature during over night and diluted with 50 ml of dichloromethane, and the organic layer was washed successively with dilute hydrochloric acid, 1N aqueous sodium hydroxide solution and then water, and dried over sodium sulfate. The solvent was distilled away, and the resultant crude desired product was purified by silica gel chromatography using hexane/ethyl acetate as a solvent to give 1.3 g of the desired product.

6) Preparation of 4-hydroxy-(1-trifluoromethyl-6-ethoxyhexyloxycarbonyl)benzene 1.3 g of the compound obtained in the above 5) was dissolved in 30 ml of ethanol, and 0.8 g of benzylamine was added dropwise. Further, after stirring at room temperature for a whole day and night, the mixture was diluted with 50 ml of dichloromethane, and the mixture was washed successively with dilute hydrochloric acid and then water, and dried over sodium sulfate. The solvents were distilled away, and the residue was subjected to isolation and purification by silica gel column chromatography to give 1.0 g of the desired product.

7) Preparation of 4'-(trifluoromethyl-6-ethoxy-hexyloxycarbonyl)phenyl ester of 4-(5-n-octyl-1,3-dioxan-2-yl)benzoic acid.

Figure 1:
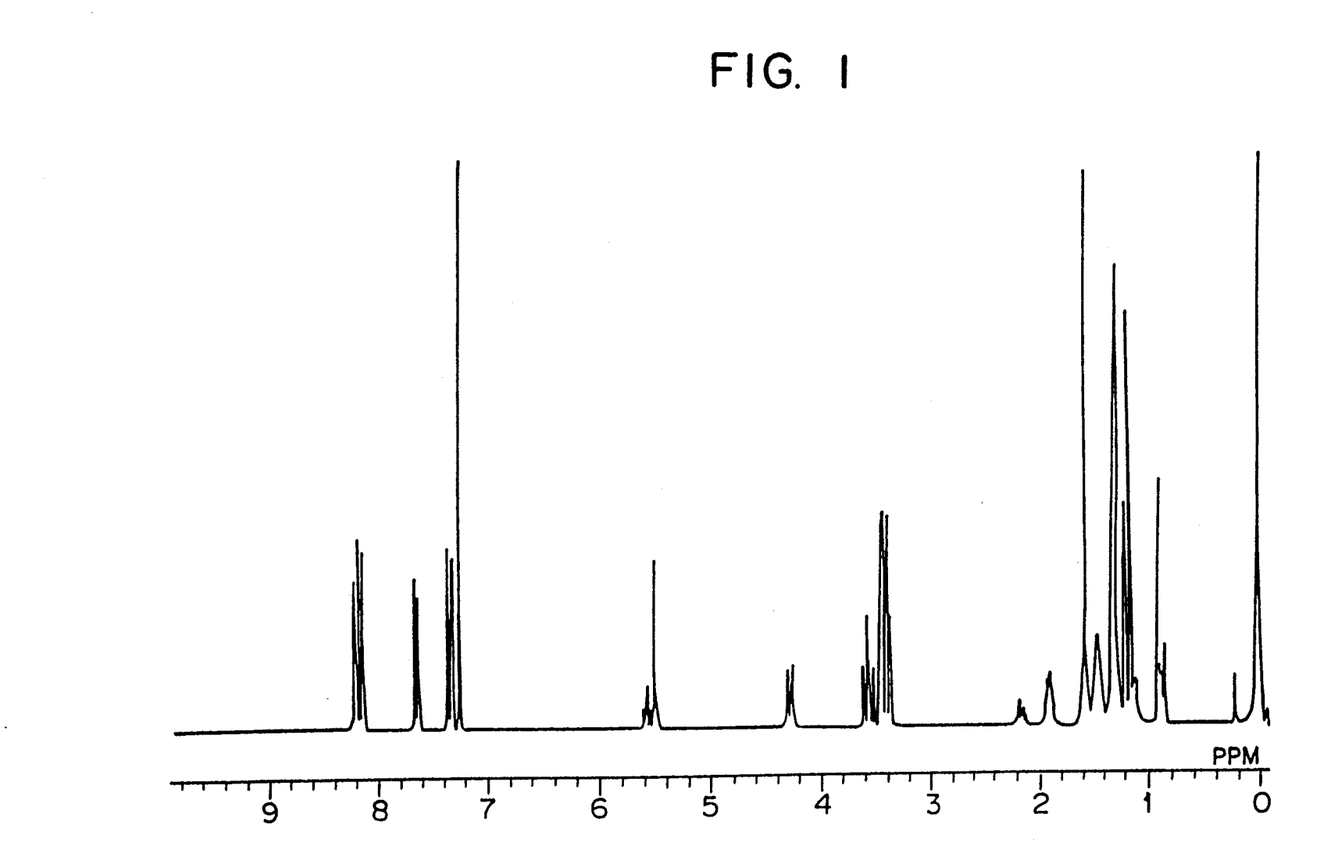
FIG. 1 is a drawing showing the NMR spectrum of the liquid crystal substance obtained in Example 1.

10 ml of thionyl chloride was added to 0.9 g of the benzoic acid derivative obtained in 4), and the mixture was refluxed with heating for 5 hours. After the excess thionyl chloride was distilled away, 2 ml of pyridine and 15 ml of toluene were added, 0.6 g of the compound obtained in the above 6) was added dropwise, and the mixture was subjected to reaction at room temperature for a whole day and night. After completion of the reaction, the reaction mixture was diluted with 50 ml of dichloromethane, washed successively with dilute hydrochloric acid, 1N aqueous sodium carbonate solution and then water, and the organic layer was dried over sodium sulfate. Then, after the solvents were distilled away, the residue was subjected to separate by silica gel chromatography to give 1.1 g of the finally desired product. The NMR spectrum of the desired product is shown in FIG. 1. Identification of the phase of this compound was carried out by texture observation and measurement of DSC. Further, measurement of the melting point was carried out by DSC and the value was 46° C.

Further, the phase sequence of this compound was as follows. Is was recognized that an anti-ferroelectric phase existed in this compound and this compound was a liquid crystal substance having an anti-ferroelectric phase.

In the above phase sequence, SA represents a smectic A state and SCA* represents an anti-ferroelectric phase. Further, SX is an unidentified phase.

Figure 2:
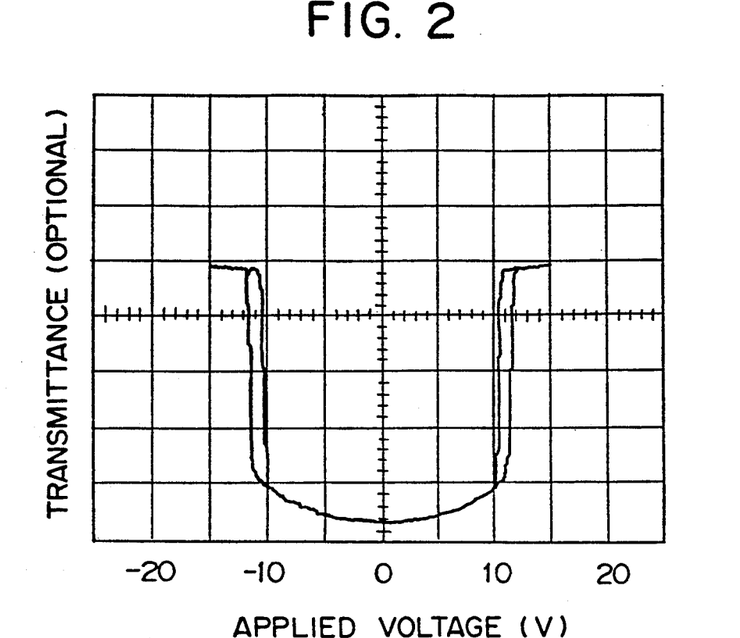
FIG. 2 is a drawing showing the optical response histeresis of the liquid crystal substance obtained in Example 1.

8) The liquid crystal substance obtained in the above 7) was filled in an isotropic state into a liquid crystal cell (cell thickness: 2 μm) having a rubbing-treated polyimide thin film and equipped with ITO electrodes. This cell was gradually cooled at a rate of 1.0° C. per minute and thereby the liquid crystal was aligned in the SA phase. The cell was arranged between deflecting plates crossing at right angles so that the direction of the layer of the liquid crystal became parallel to the analyzer or the polarizer, triangle wave voltage of ±40 V, and 0.2 Hz was applied to the cell, and change in transmittance was measured by a photomultiplier. As a result, double hysteresis peculiar to an anti-ferroelectric phase was recognized in the temperature region from 65° C. to 10° C. Optical response hysteresis at 40° C. is shown in FIG. 2.

Further, a step voltage of 35 V and 30 Hz was applied to the above liquid crystal cell, a time to be required for the change in transmittance from 10 to 90% was defined as response time, and response speed was measured. As a result, at 25° C., the change from the anti-ferroelectric phase to the ferroelectric phase took 22μ seconds and the change from the ferroelectric phase to the anti-ferroelectric phase took 18μ seconds, and thus the liquid crystal substance exhibited extremely high speed response.

EXAMPLE 2

Preparation of 4'-(1-trifluoromethyl-6-ethoxyhexyloxycarbonyl)phenyl ester of 4-(5-n-octyloxy-1,3-dioxan-2-yl)benzoic acid [in case of R=n-$C_{18}H_{17}$, X=0, L=5, m=1 and n=2 in the general formula (I)].

(1) Preparation of 2-octyloxy-1,3-propanediol 0.6 ml of concentrated sulfuric acid was added to 165 g of 1-octanol, the mixture was stirred at room temperature and 23.5 g of glycidol was added dropwise. The reaction mixture was poured on ice water, the mixture was neutralized with 1N aqueous sodium hydroxide solution and extracted with ether, and the ether layer was dried over anhydrous sodium sulfate. The solvent was distilled away, the most part of 1-octanol was removed by vacuum distillation, and the residue was distilled under a vacuum of 1 mmHg to give 10.3 g of the desired product containing a by-product 3-octyloxy-1,2-propanediol.

(2) Preparation of 4-(5-octyloxy-1,3-dioxan-2-yl)benzonitrile

To 10.2 g of the diol mixture obtained in (1) were added 100 ml of benzene, 6.6 g of p-cyanobenzaldehyde and p-toluenesulfonic acid monohydrate, and the mixture was heated. The generated water was removed by azeotropy with benzene. Then, the remaining benzene was distilled away, 200 ml of aqueous saturated sodium bicarbonate solution was added to the residue, and the mixture was extracted with dichloromethane. The extract was washed twice with water and dried over anhydrous sodium sulfate, and the solvent was distilled away to give 15.5 g of a crude product containing a by-product 4-(4-octyloxymethyl-1,3-dioxolan-2-yl)benzonitrile. This crude product was treated by column chromatography using silica gel to give 1.4 g of the desired product.

(3) Preparation of 4-(5-octyloxy-1,3-dioxan-2-yl)benzoic acid 1 g of potassium hydroxide, 1.5 ml of water and 60 ml of ethylene glycol were added to 1.4 g of the benzonitrile derivative obtained in (2), and the mixture was refluxed for 5 hours. After the mixture was allowed to cool, an equal volume of water was added, 1N hydrochloric acid was then added until the pH became 1, and the mixture was stirred under ice cooling for 1 hour. The deposited solid was filtered and dissolved in ether and the solution was dried over anhydrous sodium sulfate. The solvent was then removed to give 1.4 g of the desired product.

(4) Preparation of 4-hydroxy-(1-trifluromethyl-6-ethoxy-hexyloxycarbonyl)benzene Utterly the same procedures as in 5) and 6) of Example 1 were carried out to prepare the desired product.

Figure 3:
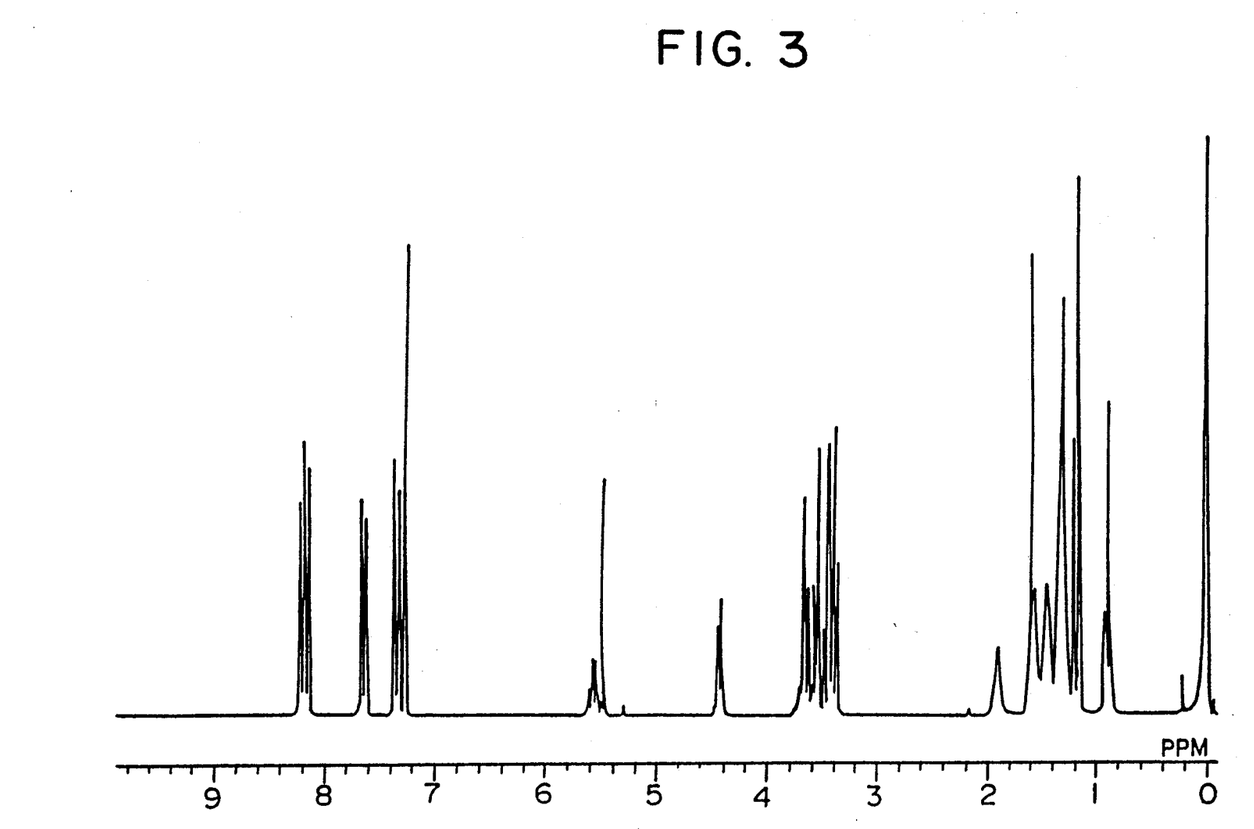
FIG. 3 is a drawing showing the NMR spectrum of the liquid crystal substance obtained in Example 2.

(5) Preparation of 4'-(1-trifluromethyl-6-ethoxy-hexyl-oxycarbonyl)phenyl ester of 4-(5-n-octyloxy-1,3-dioxan-2-yl)benzoic acid Utterly the same procedures as in 7) of Example 1 were carried out except that 4-(5-octyloxy-1,3-dioxan-2-yl)acetic acid prepared in (3) of this example was used in place of 4-(5-octyl-1,3-dioxan-2-yl)benzoic acid used in 7) of Example 1, whereby the desired product was prepared. The NMR spectrum of the desired product is shown in FIG. 3. Identification of the phase was carried out by texture observation and measurement of DSC. Further, measurement of the melting point was carried out by DSC and the value was 53° C.

The phase sequence of this compound was as follows. It was recognized that an anti-ferroelectric phase exists in this compound and this compound was a liquid crystal substance having an anti-ferroelectric phase.

In the above phase system, SX is an unidentified phase.

Figure 4:
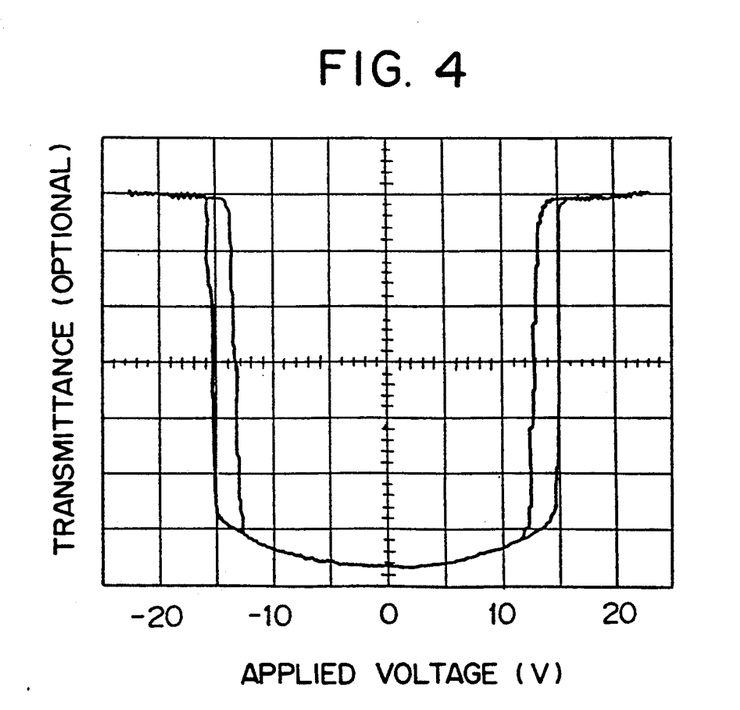
FIG. 4 is a drawing showing the optical response histeresis of the liquid crystal substance obtained in Example 2.

(6) The optical response of the compound obtained in the above (5) was investigated in the same manner as in 8) of Example 1, and as a result double hysteresis peculiar to the anti-ferroelectric phase was recognized in the temperature region of 40° to 25° C. Optical response hysteresis at 30° C. is shown in FIG. 4. Further, response speed was measured in the same manner as in 8) of Example 1, and as a result, at 36° C., the change from the anti-ferroelectric phase to the ferroelectric phase took 29μ seconds and the change from the ferroelectric phase to the anti-ferroelectric phase took 32μ seconds, and thus the liquid crystal substance exhibited extremely high speed response.

EXAMPLE 3

Preparation of 4'-(1-trifluoromethyl-heptyloxycarbonyl)phenyl ester of 4-(5-n-octyloxy-1,3-dioxan-2-yl)benzoic acid [in case of R=n-C$_8$H$_{17}$, X=0, L=0, m=0 and n=6 in the general formula (I)]

Figure 5:
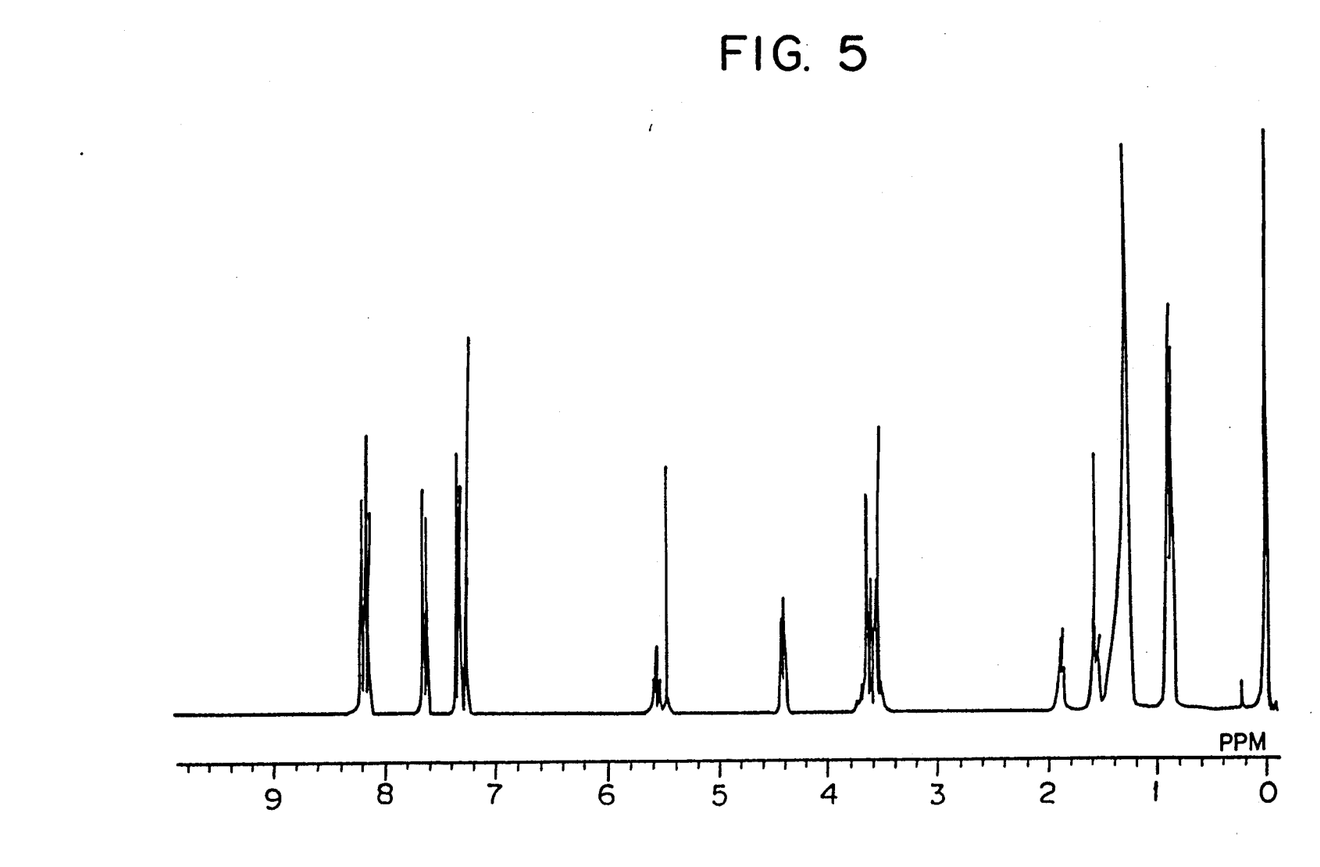
FIG. 5 is a drawing showing the NMR spectrum of the liquid crystal substance obtained in Example 3.

Utterly the same procedures as in Example 2 were carried out using R-(+)-1,1,1-trifluoro-2-octanol in place of R-(+)-1,1,1-trifluoro-7-ethoxy-2-heptanol in Example 2, whereby was prepared 4'-(1-trifluoromethylheptyloxycarbonyl)phenyl ester of 4-(5-n-octyloxy-1,3-dioxan-2-yl)benzoic acid. The NMR spectrum of the desired product is shown in FIG. 5. Identification of the phase was carried out by texture observation and measurement of DSC. Further, measurement of the melting point was carried out by DSC.

The phase sequence of this compound was as follows. In this compound, an anti-ferroelectric phase was recognized, the phase sequence was as follows and the melting point was 83° C.

$$\text{Crystal} \xleftrightarrow{42°\text{C.}} \text{SCA}^* \xleftrightarrow{64°\text{C.}} \text{SA} \xleftarrow{68°\text{C.}} \text{Isotropic phase}$$

Figure 6:
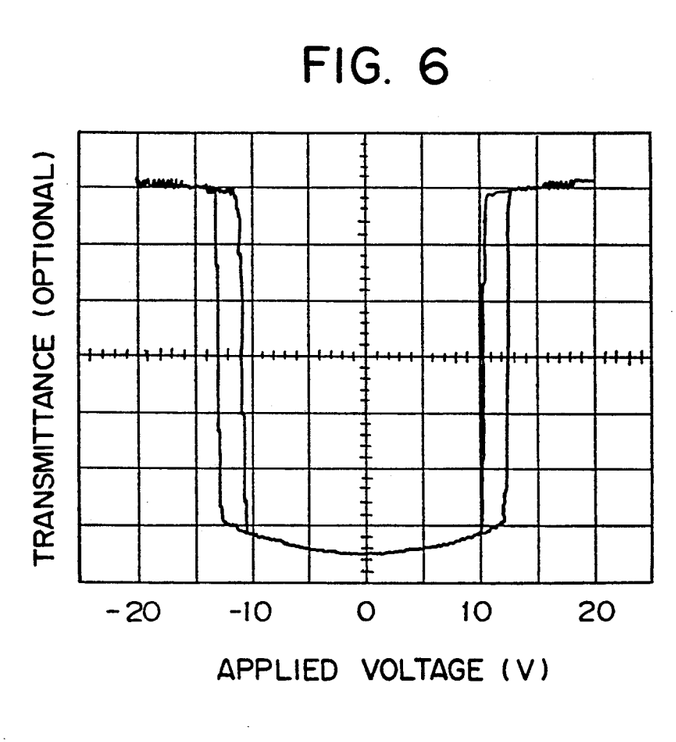
FIG. 6 is a drawing showing the optical response histeresis of the liquid crystal substance obtained in Example 3.

Further, optical response against electric fields was investigated in the same manner as in 8) of Example 1, and as a result double hysteresis peculiar to the anti-ferroelectric phase was recognized in the temperature range of 63° to 39° C. as shown in FIG. 6. Further, response speed was measured in the same manner as in 8) of Example 1, and as a result, at 58° C., the change from the anti-ferroelectric phase to the ferroelectric phase took 10μ seconds and the change from the ferroelectric phase to the anti-ferroelectric phase took 8μ seconds, and thus this compound exhibited high speed response.

We claim:

1. Anti-ferroelectric liquid crystal compounds represented by the following formula (I)

wherein
R represents a straight-chain alkyl group having 6 to 10 carbon atoms;
X represents an oxygen atom or a single bond;
provided that, when X is an oxygen, L is an integer of 5 to 8, m is 1 and n is an integer of 1 to 7, or L and m are zero and n is an integer of 6 to 8; and, when X is single bond, L is an integer of 5 to 8, m is 1 and n is an integer of 1 to 7; and
C* represents an asymmetric carbon atom.

2. The liquid crystal compounds of claim 1 wherein R is a straight-chain alkyl group having 6 to 10 carbon atoms.

3. The liquid crystal compounds of any of claims 2 or 1 wherein X is an oxygen atom, L is an integer of 5 to 8, m is 1 and n is an integer of 1 to 7.

4. The liquid crystal compounds of any of claims 2 or 8 wherein X is an oxygen atom, L is zero, m is zero and n is an integer of 6 to 8.

5. The liquid crystal compounds of any of claims 2 or 1 wherein X is a single bond, L is an integer of 6 to 10, m is 1 and n is an integer of 1 to 7.

6. A liquid crystal display device wherein a liquid crystal compound of claim 1 is used.

* * * * *